United States Patent
Lee et al.

(10) Patent No.: US 11,254,645 B2
(45) Date of Patent: Feb. 22, 2022

(54) METHOD FOR PREPARING TOLIMIDONE ON LARGE SCALE

(71) Applicant: BUKWANG PHARMACEUTICAL CO., LTD., Seoul (KR)

(72) Inventors: Kwang Ok Lee, Gyeonggi-Do (KR); Kyung Hwa Lee, Seoul (KR); Eun Ju Jeong, Seoul (KR)

(73) Assignee: BUKWANG PHARMACEUTICAL CO., LTD., Seoul (KR)

( * ) Notice: Subject to any disclaimer, the term of this patent is extended or adjusted under 35 U.S.C. 154(b) by 44 days.

(21) Appl. No.: 16/960,796

(22) PCT Filed: Jan. 11, 2018

(86) PCT No.: PCT/KR2018/000530
§ 371 (c)(1),
(2) Date: Jul. 8, 2020

(87) PCT Pub. No.: WO2019/139185
PCT Pub. Date: Jul. 18, 2019

(65) Prior Publication Data
US 2021/0061772 A1 Mar. 4, 2021

(51) Int. Cl.
*C07D 239/52* (2006.01)
(52) U.S. Cl.
CPC ........ *C07D 239/52* (2013.01); *C07B 2200/13* (2013.01)
(58) Field of Classification Search
CPC .................................................. C07D 239/52
See application file for complete search history.

(56) References Cited

U.S. PATENT DOCUMENTS 3,922,345 A * 11/1975 Lipinski ............... C07D 239/52
514/269

FOREIGN PATENT DOCUMENTS

| KR | 10-2016-0065496 A | | 6/2016 |
| KR | 10-1827744 B1 | | 2/2018 |
| WO | WO2013-090319 | * | 6/2013 |
| WO | WO-2013-090319 A2 | | 6/2013 |

OTHER PUBLICATIONS

Iacocca, et al. (2010) "Particle Engineering: A Strategy for Establishing Drug Substance Physical Property Specifications During Small Molecule Development." *Journal of Pharmaceutical Sciences*, 99(1):51-75.
Ochman, et al. (2012) "The Lyn Kinase Activator MLR-1023 Is a Novel Insulin Receptor Potentiator that Elicits a Rapid-Onset and Durable Improvement in Glucose Homeostasis in Animal Models of Type 2 Diabetes." *The Journal of Pharmacology and Experimental Therapeutics*, 342(1):23-32.
Mosharraf, et al. (1995) "The effect of particle size and shape on the surface specific dissolution rate of microsized practically insoluble drugs." *International Journal of Pharmaceutics*, 122(12):35-47.
Lipinski, C. A. et al. "Bronchodilator and Antiulcer Phenoxypyrimidinones[1]." *J. Med. Chem.*, 1980, vol. 23, No. 9, pp. 1026-1031.
International Search Report issued in International Patent Application No. PCT/KR2018/000530, dated Oct. 11, 2018.

* cited by examiner

*Primary Examiner* — Valerie Rodriguez-Garcia
(74) *Attorney, Agent, or Firm* — Harness, Dickey & Pierce, P.L.C.

(57) ABSTRACT

The present disclosure relates to a method for preparing tolimidone on large scale with maintaining high purity and uniform particle size distribution, and more specifically, a method suitable for preparing tolimidone on industrially large scale by using tetrabutyl ammonium bromide catalyst and recrystallization in ethanol, which can prepare highly pure tolimidone in a time shorter than prior arts while maintaining water content and particle size distribution constantly.

13 Claims, 1 Drawing Sheet

[Fig. 1]
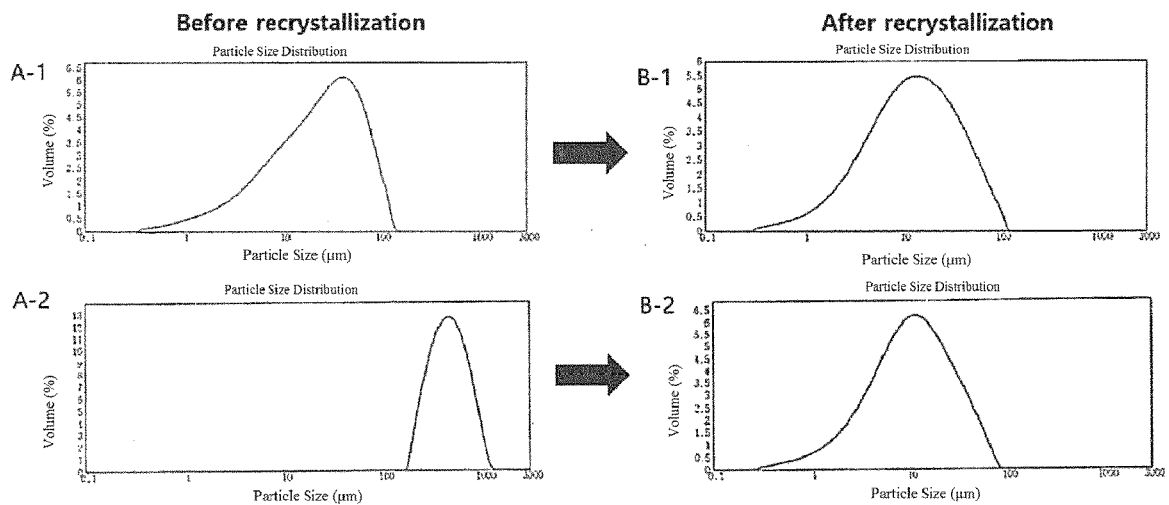
[Fig. 2]
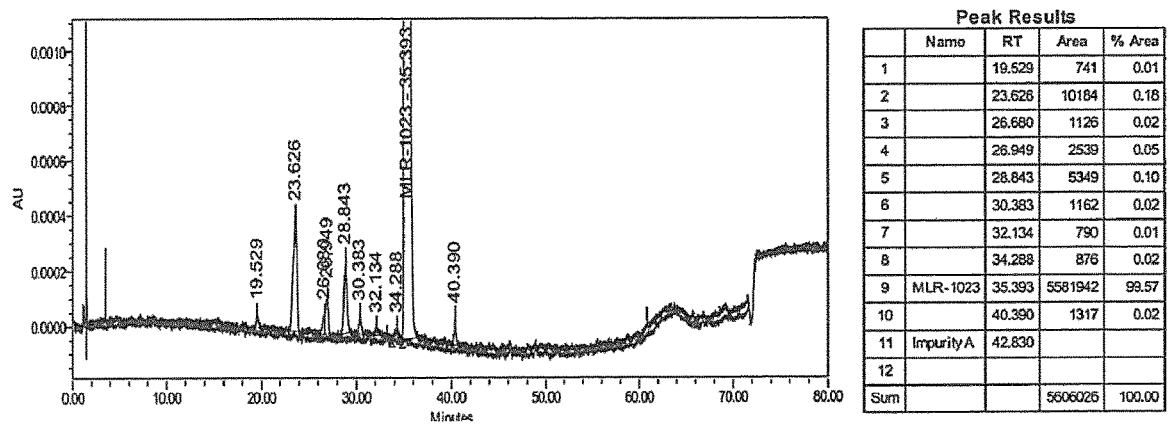
[Fig. 3]
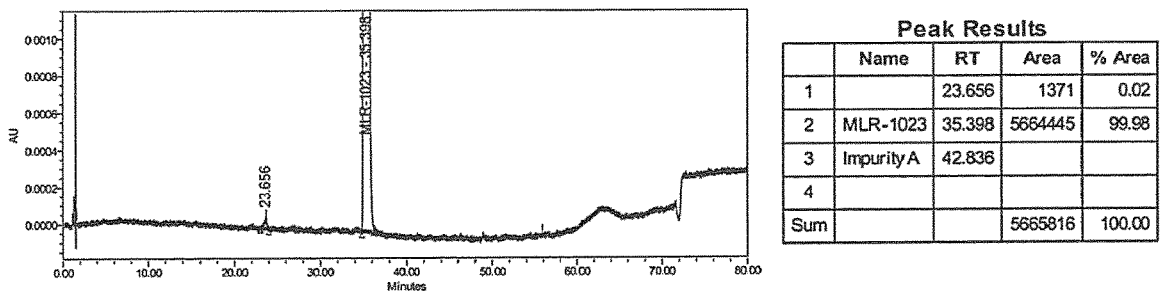

METHOD FOR PREPARING TOLIMIDONE ON LARGE SCALE

CROSS-REFERENCE TO RELATED APPLICATIONS

This application is a national phase application of PCT Application No. PCT/KR2018/000530, filed on Jan. 11, 2018. The entire disclosure of the application identified in this paragraph is incorporated herein by reference.

TECHNICAL FIELD

The present disclosure relates to a method for preparing tolimidone on large scale with maintaining high purity and uniform particle size distribution, and more specifically, a method suitable for preparing tolimidone on industrially large scale by using tetrabutyl ammonium bromide catalyst and recrystallization in ethanol, which can prepare highly pure tolimidone in a time shorter than prior arts while maintaining water content and particle size distribution constantly.

BACKGROUND ART

Tolimidone of the following formula 1 exhibits good effect of lowering blood sugar in diabetes-induced animal model through the mechanism of action of lowering blood sugar by activating Lyn kinase (The Journal of Pharmacology and Experimental Therapeutics, 2012, Vol. 342, No. 1, pp. 23-32).

[Formula 1]

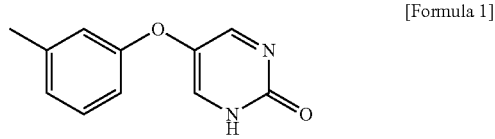

In the currently known method for preparing tolimidone, as shown in the following reaction scheme 1, the compounds of formulas 6 and 5 as starting materials are reacted to obtain the intermediate of formula 4, and then the aldehyde intermediate of formula 3 is obtained through Vilsmeir reaction. Next, the intermediate of formula 3 and urea are refluxed with agitation under the condition of sodium ethoxide/ethanol to obtain the sodium salt of formula 2, and then the sodium metal is desalted by using 6N aqueous solution of hydrochloric acid or acetic acid to obtain tolimidone of formula 1 (U.S. Pat. No. 3,922,345; Journal of Medicinal Chemistry, 1980, Vol. 23, pp. 1026-1031).

[Reaction scheme 1]

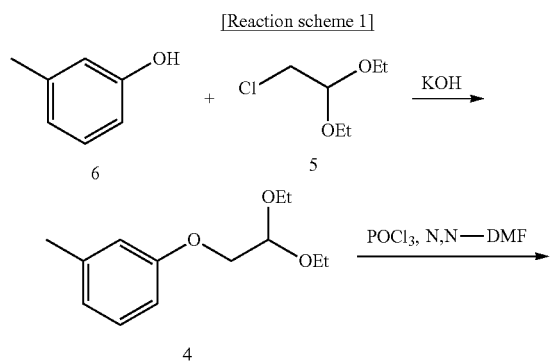

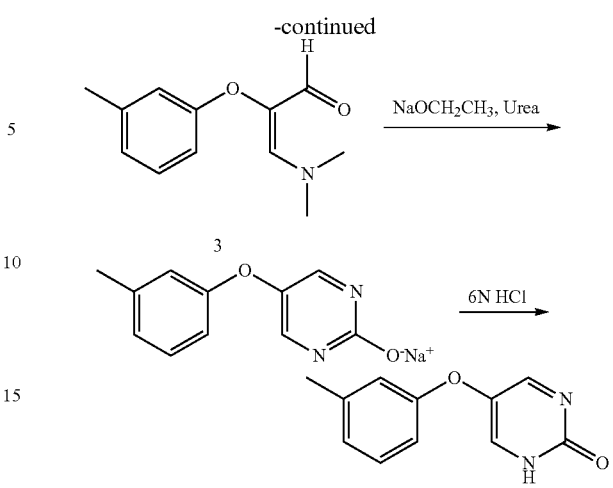

However, in case of the first reaction of the above preparation method, in order to obtain the intermediate of formula 4, water should be removed from meta-cresol of formula 6 and the starting material of formula 5 in the presence of potassium hydroxide in Dean-Stark apparatus at a high temperature of 140~150° C., and this procedure is not suitable for a large scale production process.

Next, in the step of desalting the sodium salt of formula 2 by using hydrochloric acid or acetic acid to obtain tolimidone of formula 1, it is not easy to completely remove water, which is used for washing in filtering procedure of a large scale production process, through drying procedure. In addition, the particle size distribution of tolimidone of formula 1 obtained by the above preparation method is not sufficiently uniform for large scale production, and the reproducibility of the particle size distribution is also not sufficient for large scale production.

It has been generally known that particle size distribution of a drug affects the dissolution rate, bioavailability, stability, etc. of the drug (JOURNAL OF PHARMACEUTICAL SCIENCES 2010, 99 (1), 51~75; INTERNATIONAL JOURNAL OF PHARMACEUTICS 1995, 122 (1-2), 35~47). Therefore, the uniform particle size distribution of tolimidone of formula 1 is very important in order to uniformly maintaining the dissolution rate, bioavailability, etc. of the drug in clinical use.

DISCLOSURE OF INVENTION

Technical Problem

A purpose of the present disclosure is the provision of a suitable method for preparing highly pure tolimidone on large scale while maintaining water content and particle size distribution constantly.

Another purpose of the present disclosure is the provision of a pharmaceutical composition comprising tolimidone prepared by the method disclosed herein.

Solution to Problem

To achieve the above-stated purposes, the present disclosure provides a method for preparing tolimidone, comprising:
(i) reacting the compound of formula 6 and the compound of formula 5 in the presence of a tetra-substituted ammonium salt catalyst to prepare the compound of formula 4;

(ii) conducting Vilsmeir reaction for the prepared compound of formula 4 to prepare the compound of formula 3;

(iii) refluxing with agitation the prepared compound of formula 3 together with urea and an alkoxide base to prepare the salt compound of formula 2; and (iv) desalting the prepared salt compound of formula 2 to obtain tolimidone of formula 1 and recrystallizing the obtained tolimidone with an alcohol that corresponds to the alkoxide base:

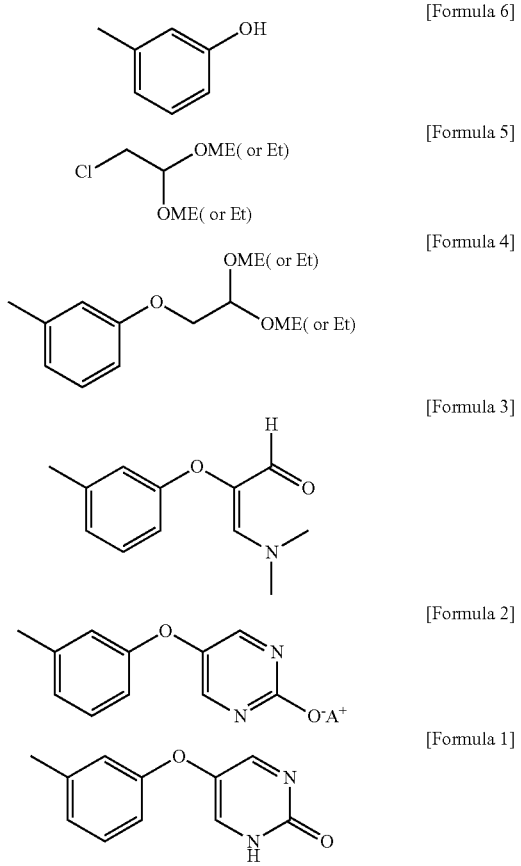

wherein $A^+$ is a cation of the alkoxide base.

In addition, the present disclosure provides a pharmaceutical composition comprising tolimidone prepared by the above method and a pharmaceutically acceptable carrier.

The present disclosure is explained in more detail below.

In step (i) of the method for preparing tolimidone according to the present invention, the compound of formula 4 is prepared by reacting the starting materials of meta-cresol of formula 6 and dimethyl (or ethyl) chloroacetaldehyde of formula 5 in the presence of a tetra-substituted ammonium salt, such as a tetra-alkyl ammonium salt, such as a tetra-alkyl ammonium halide salt, such as tetrabutyl ammonium bromide catalyst. The tetra-substituted ammonium salt catalyst reaction is preferably conducted in a hydrocarbon solvent, such as an aromatic hydrocarbon solvent, such as toluene solvent in the presence of a hydroxide base, such as potassium hydroxide.

In the known method, the compound of formula 6 and the compound of formula 5 are reacted in Dean-Stark apparatus at a high temperature of 140~150° C. for a long time—for example, the reaction is conducted for 12 to 16 hours when using about 160 g of the compound of formula 6 and about 3000 g of the compound of formula 5—and the reactant of formula 4 separated from the Dean-Stark apparatus should be fed back to the reactor at the high temperature in order to complete the reaction. Thus, this procedure is not suitable for a large scale production.

In the present disclosure, however, when using the same amounts of the compound of formula 6 and the compound of formula 5 as stated above, the reaction in the presence of tetrabutyl ammonium bromide catalyst can be completed preferably at a temperature of 100 to 120° C., more preferably at a temperature of 105 to 110° C., within about 6 hours only. Thus, the present invention is suitable for a large scale production.

In step (ii) of the method for preparing tolimidone according to the present invention, the compound of formula 3 is prepared from the compound of formula 4 through Vilsmeir reaction. The aldehyde intermediate of formula 3 can be obtained by reacting the compound of formula 4 with N,N-dimethylformamide and phosphoryl chloride.

In step (iii) of the method for preparing tolimidone according to the present invention, the sodium salt compound of formula 2 is prepared by refluxing with agitation the compound of formula 3 together with urea and an alkoxide base, such as sodium ethoxide.

In step (iv) of the method for preparing tolimidone according to the present invention, tolimidone sodium salt of formula 2 is desalted to obtain tolimidone of formula 1 and the obtained tolimidone is recrystallized with an alcohol that corresponds to the alkoxide base in step (iii), such as ethanol.

In the present disclosure, tolimidone sodium salt of formula 2 is desalted preferably by using hydrochloric acid or acetic acid. After the desalting, a step of washing with water is necessary, and after the washing, the used water should be removed through a drying step. In a small scale reaction, for example, a reaction using 15 g of the compound of formula 3, the water removal is so easy that the residual water content after vacuum drying at 65° C. for 14 hours is less than 0.1%.

However, in a large scale production of tolimidone, for example, production of tens to hundreds kg unit, perfect removal of water is difficult. In case of active pharmaceutical ingredients (APIs), maintaining the water content constantly is very important to control the product quality.

In the present disclosure, after the desalting of tolimidone sodium salt and the washing with water, without completely drying, it is recrystallized in ethanol under reflux with agitation to remove water easily.

Meanwhile, tolimidone prepared by the known method contains impurities and thus a purification process is needed. However, in the present disclosure, most of the impurities can be removed through the recrystallization in ethanol. In addition, in case of tolimidone prepared by the known method, the particle size distribution is not sufficiently uniform for large scale production and the reproducibility of the particle size distribution is also not sufficient for large scale production, and thus, when formulating as a drug, there may be problem in maintaining the dissolution rate, bioavailability, etc. uniformly. However, in the present disclosure, it is possible to make the particle size distribution uniform through the recrystallization in ethanol. The particle size distribution of tolimidone prepared according to the present invention is preferably 5~30 μm as d(0.5).

According to the other aspect of the present disclosure, a pharmaceutical composition comprising tolimidone prepared by the above method and a pharmaceutically acceptable carrier is provided.

In the present disclosure, the pharmaceutically acceptable carrier is a matrix material used for enteric purpose, and may be hydroxypropylmethylcellulose phthalate, hydroxypropylmethylcellulose acetate succinate, polyvinylacetate phthalate, celluloseacetate phthalate, poly(methacrylic acid, methylmethacrylate) copolymer, poly(methacrylic acid, ethylacrylate) copolymer, shellac, or a mixture thereof, but it is not limited to the above. Among pharmaceutically acceptable carriers, for the purpose of sustained release, components selected from hydrophobic materials and hydrophilic polymers can be used. The hydrophobic material is pharmaceutically acceptable and may be selected from polyvinyl acetate, ethylcellulose and celluloseacetate, poly (ethylacrylate, methyl methacrylate) copolymer as polymethacrylate copolymer, poly(ethylacrylate, methyl methacrylate, trimethylaminoethylmethacrylate) copolymer, fatty acids and fatty acid esters, fatty acid alcohols, waxes, etc., but it is not limited to the above. More concretely, one or more selected from glyceryl palmitostearate, glyceryl stearate, glyceryl behenate, cetyl palmitate, glyceryl mono oleate and stearic acid, etc. as the fatty acids and fatty acid esters, cetostearyl alcohol, cetyl alcohol and stearyl alcohol, etc. as the fatty acid alcohols, carnauba wax, beeswax and microcrystalline wax, etc. as the waxes may be used, but it is not limited to the above. As the hydrophilic polymer, sugars, cellulose derivative, gums, polyvinyl derivative, polymethacrylate copolymer, polyethylene derivative, carboxyvinyl polymer, etc. may be selected and used. Concretely, dextrin, polydextrin, dextran, pectin and pectin derivative, alginate, polygalaturonic acid, xylane, arabinoxylane, arabinogalactan, starch, hydroxypropylstarch, amylose, amylopectin, etc. may be selected and used as the sugar; hydroxypropylmethylcellulose, hydroxypropylcellulose, hydroxymethylcellulose, hydroxyethylcellulose, methylcellulose, carboxymethylcellulose sodium, hydroxypropyl methylcellulose acetate succinate, hydroxyethylmethylcellulose, etc. may be selected and used as the cellulose derivative; gua gum, locust bean gum, tragacanth, carrageenan, acacia gum, arabic gum, gellan gum, xanthan gum, etc. may be selected and used as the gum; polyvinyl alcohol, polyvinyl pyrrolidone, polyvinylacetaldiethylaminoacetate, etc. may be selected and used as the polyvinyl derivative; poly(butyl methacrylate, (2-dimethylaminoethyl)methacrylate, methylmethacrylate) copolymer, etc. may be selected and used as the polymethacrylate copolymer; polyethylene oxide, etc. may be selected and used as the polyethylene derivative; and carbomer may be selected and used as the carboxyvinyl polymer; but it is not limited to the above. In addition, if necessary, the pharmaceutical composition according to the present disclosure may further comprise, for example, diluent, binder, disintegration agent, fluidizing agent, pH controlling agent, etc.

The pharmaceutical composition according to the present disclosure exhibits good effect of lowering blood sugar, and thus it can be effectively used in prevention or treatment of diabetes.

Advantageous Effects of Invention

The method for preparing tolimidone of the present disclosure improves the reaction at a high temperature for a long time to be conducted at a lower temperature for an effectively reduced time, and thus is very suitable for large scale production of tolimidone. According to the present disclosure, highly pure tolimidone with low water content can be prepared while maintaining particle size distribution constantly.

BRIEF DESCRIPTION OF DRAWINGS

FIG. 1 shows the results of analyzing the particle size distribution of tolimidone before/after the recrystallization in ethanol.

FIG. 2 shows the results of HPLC analysis for measuring the purity of tolimidone prepared in Comparative Example 3.

FIG. 3 shows the results of HPLC analysis for measuring the purity of tolimidone prepared in Example 4 after the recrystallization in ethanol.

MODE FOR THE INVENTION

The present disclosure is explained in more detail by the following examples. However, these examples seek to illustrate the present disclosure only for facilitating the understanding of the present disclosure, and the scope of the present disclosure is not limited by the examples in any manner.

Example 1-1

Small Scale Preparation of
1-(2,2-dimethoxyethoxy)-3-methylbenzene
(Tetrabutyl Ammonium Bromide Catalyst Reaction)

In a 1,500 mL reaction flask, meta-cresol (165 g, 1.53 mol) and toluene (330 mL) were fed, and then tetrabutyl ammonium bromide (49.5 g) was added thereto. Subsequently, potassium hydroxide (85%, 100.7 g) was slowly added, and chloroacetaldehyde dimethylacetal (302.1 g) was added thereto. The reaction temperature was elevated to 110° C. and the mixture was refluxed with agitation. After reacting for 6 hours, the termination of the reaction was confirmed through TLC. After cooling the reaction mixture to room temperature, the toluene layer was separated and washed with 300 mL of 5% aqueous solution of sodium hydroxide, and then washed with 300 mL of brine. Subsequently, 30 g of magnesium sulfate was added to the organic layer to remove water, and then filtered. The organic solvent was evaporated under reduced pressure to obtain the target compound (278.4 g, 93%).

$^1$H-NMR 500 MHz (CDCl$_3$): 7.15 (m, 1H), 6.75 (m, 3H), 4.68 (t, 1H), 3.97 (d, 2H), 3.40 (s, 6H), 2.29 (s, 3H).

Example 1-2

Large Scale Preparation of
1-(2,2-dimethoxyethoxy)-3-methylbenzene
(Tetrabutyl Ammonium Bromide Catalyst Reaction)

In a reactor, meta-cresol (72.5 kg) was fed, and with agitation potassium hydroxide (125.43 kg) was added thereto. Subsequently, tetrabutyl ammonium bromide (21.75 kg) and toluene (145 L) were added thereto. After adding chloroacetaldehyde dimethylacetal (135.58 kg), while maintaining the reaction temperature at 105° C. or higher, the mixture was refluxed with agitation for 22 hours (The termination of the reaction was confirmed after 6 hours). The inside of the reactor was cooled to 15~25° C. and purified water (363 L) was added thereto, and after agitation for 30 minutes, the underlying aqueous layer was transferred to another reactor. To the reactor containing the aqueous layer, toluene (145 L) was added, and after the extraction, the organic layers were collected. Sodium sulfate (72.5 kg) and silica gel (72.5 kg) were added thereto and agitated for 1 hour or longer. Subsequently, after filtering through a filter device, the filtrate was transferred to a reactor. While maintaining the inside of the reactor at 65° C. or lower, the filtrate was evaporated under reduced pressure to obtain 118 kg of the target compound.

Comparative Example 1

Preparation of 1-(2,2-dimethoxyethoxy)-3-methylbenzene (Using Dean-Stark Apparatus)

In a 1,000 mL reaction flask, meta-cresol (160 g, 1.48 mol) was fed and with agitation, potassium hydroxide (85%, 107.4 g) was slowly added, the mixture was agitated at 100~130° C. for 1 hour to completely dissolve potassium hydroxide, and chloroacetaldehyde dimethylacetal (298.8 g) was slowly added dropwise thereto. While maintaining the temperature of the reaction mixture at 140~150° C. and conducting the reaction for 16 hours, the aqueous layer was removed and the organic layer was fed back to the reaction mixture by using Dean-Stark apparatus. After confirming the termination of the reaction through TLC and cooling the reaction mixture to room temperature, 300 mL of toluene and 400 mL of purified water were added thereto. The organic layer was separated and washed with 200 mL of 5% aqueous solution of sodium hydroxide, and then washed with 200 mL of brine. Subsequently, 30 g of magnesium sulfate was added to the organic layer to remove water, and then filtered. The organic solvent was evaporated under reduced pressure to obtain the target compound (272 g, 94%).

Example 2

Large Scale Preparation of (E)-3-(dimethylamino)-2-(meta-tolyloxy)acrylaldehyde

In a reactor, 246.5 kg of chloroform was fed and 131.95 kg of N,N-dimethylformamide was added thereto. While maintaining the temperature of the reaction mixture at 30° C. or lower, phosphoryl chloride (277.68 kg) was slowly added dropwise thereto. After the dropwise addition, the reaction mixture was agitated at 55° C. for 2 hours. To the reaction mixture, 1-(2,2-dimethoxyethoxy)-3-methylbenzene obtained in Example 1-2 was slowly added dropwise, and the reaction mixture was refluxed with agitation for 2 hours while maintaining the temperature of the reaction mixture at 65~70° C. Subsequently, 145 L of toluene was added thereto and the reaction mixture was cooled to 10° C. or lower. To another reactor, inside of which was maintained at 10° C. or lower, 580 L of purified water was fed, and the reaction mixture was slowly added dropwise thereto. At that time, the inside temperature was maintained at 50° C. or lower. 435 L of toluene was additionally added to the reactor, and an aqueous solution of potassium hydroxide (836.65 kg of potassium hydroxide dissolved in 1,367 L of purified water) was slowly added dropwise thereto. After agitation for 1 hour, the organic layer was separated and washed with 500 L of 10% brine. Sodium sulfate (72.5 kg) and silica gel (72.5 kg) were added to the organic layer, and the mixture was agitated for 1 hour and then filtered. The filtrate was evaporated under reduced pressure to remove the organic solvent, and 136 L of ethyl acetate was added to the concentrated residue. Subsequently, heptane (29.73 kg) was added thereto and the mixture was agitated at the inside temperature of 15~25° C. for 2 hours or longer. The reaction mixture was cooled to 0° C., and after agitation for 1 hour, the generated solid was filtered and dried under vacuum to obtain the target compound (80.9 kg).

$^1$H-NMR 500 MHz (Acetond-d6): 8.79 (s, 1H), 7.12 (m, 1H), 6.92 (s, 1H), 6.68~6.76 (m, 3H), 3.08 (s, 6H), 2.27 (s, 3H).

Example 3

Large Scale Preparation of Tolimidone Sodium Salt

In a reactor, (E)-3-(dimethylamino)-2-(meta-tolyloxy)acrylaldehyde (126 kg), urea (110.9 kg) and ethanol (99.5%) (99.5 kg) were fed and agitated for 10 minutes or longer. While maintaining the temperature of the inside of the reactor at 15~25° C., sodium ethoxide (21% in ethanol) (688 kg) was added thereto. The temperature of the inside of the reactor was elevated to 70° C., and the reaction mixture was refluxed with agitation for 4 hours. Subsequently, 16.4 L of purified water was added thereto and the reaction mixture was agitated for 3 hours. The temperature of the inside of the reactor was lowered to 15~25° C., and the generated solid was filtered and dried under vacuum at 65° C. for 14 hours to obtain tolimidone sodium salt (78.13 kg, 56.8%).

COMPARATIVE EXAMPLE 2

Small Scale Preparation of Tolimidone Sodium Salt

In a reactor, urea (8.78 g, 0.146 mol) was fed and then sodium ethoxide (21% in ethanol, 54.6 mL, 0.146 mol) was slowly added thereto. Subsequently, (E)-3-(dimethylamino)-2-(meta-tolyloxy)acrylaldehyde (15.0 g, 0.073 mol) was slowly added thereto, and the reaction mixture was refluxed with agitation for 2 hours at about 77° C. 2.65 mL of purified water was added to the reaction mixture and additionally agitated for 2 hours at about 77° C. The reaction mixture was slowly cooled to room temperature, and the generated solid was filtered to obtain tolimidone sodium salt (9.84 g, 60%).

Example 4

Large Scale Preparation of Tolimidone

To 1,659 L of purified water, tolimidone sodium salt (78.13 kg) was added and dissolved by elevating the temperature to 60° C., and then acetic acid (26.5 kg) was slowly added thereto. After cooling the inside temperature to 15~25° C., the generated solid was filtered and washed with 630 L of purified water. In spite of subsequent drying under vacuum at 65° C. for 32 hours, the water content of the obtained tolimidone (57.23 Kg) was 4%. Subsequently, the dried tolimidone was fed into a reactor, 994 L of ethanol (99.5%) was added thereto, and the temperature was elevated to 70° C. for dissolution. The temperature was slowly lowered to 15~25° C. and recrystallization was conducted with agitation for 2 hours. The reaction mixture was cooled to 0° C., agitated for 1 hour, and then filtered. After drying under vacuum in an oven at 65° C. for 14 hours, the target compound (44.7 kg, 63%) was obtained.

$^1$H-NMR 500 MHz (DMSO-$d_6$): 12.01 (s, 1H), 8.30 (m, 2H), 6.79~7.25 (m, 4H), 2.28 (s, 3H).

Comparative Example 3

Small Scale Preparation of Tolimidone

Tolimidone sodium salt obtained in Comparative Example 2 was dissolved in 150 mL of purified water with agitation at 60° C. After complete dissolution, acetic acid was added thereto dropwise to precipitate crystals at about pH 6.0. After cooling the reaction mixture to room temperature slowly, the precipitated crystals were filtered and washed with 130 mL of purified water. Subsequently, the obtained crystals were dried under vacuum in an oven at 65° C. for 14 hours to obtain 7.6 g of tolimidone (yield: 85.6%).

Comparative Example 4

Repetition of Comparative Examples 2 and 3

Comparative Examples 2 and 3 were repeated in the same manner to obtain 7.4 g of tolimidone (yield: 50.1%).

Example 5

Recrystallization in Ethanol 5.0 g of tolimidone obtained in Comparative Examples 3 and 4 was dissolved in 40 mL of ethanol under reflux with agitation, cooled to room temperature slowly, agitated for 2 hours, and filtered to obtain the respective target compound (4.2 g, 4.3 g).

Experimental Example 1

Water Content Measurement

Tolimidone prepared on small scale (Comparative Example 3), tolimidone prepared on large scale (Example 4) and tolimidone after recrystallization in ethanol were dried in an oven at 65° C. and the water contents were measured. The results are shown in the following Table 1.

TABLE 1

| | Amount of tolimidone | Drying time | Water content |
|---|---|---|---|
| 1 | 7.6 g (Comparative Example 3) | 14 hours | <0.1% |
| 2 | 57.23 kg (Example 4) | 14 hours | 36% |
| | (Before recrystallization in ethanol) | 20 hours | 29% |
| | | 26 hours | 27% |
| | | 32 hours | 4% |
| 3 | 44.7 kg (Example 4) | 14 hours | <0.1% |
| | (After recrystallization in ethanol) | | |

As can be seen from the above Table 1, in case of small scale preparation of tolimidone, the water used in desalting step could be removed easily, but in case of large scale preparation, it was not easy to remove the used water completely through drying procedure. However, the water could be removed easily through the recrystallization in ethanol even in the large scale preparation.

Experimental Example 2

Particle Size Analysis

The particle size distributions of tolimidone prepared in Comparative Examples 3 and 4 and tolimidone of Example 5 after recrystallization in ethanol were measured in a dry manner by using a particle size analyzer (AWM2000 (MAL140253), Malvern) with the following conditions, and the results are shown in the following Table 2 and FIG. 1.

Measurement:
Measurement time: 3 seconds
Measurement snaps: 3000
Background time: 5 seconds
Background snaps: 5000
Measurement Cycles (Repeats):
Aliquots: 1 per SOP
Measurements: 3 per aliquot
Delay: 5 seconds

TABLE 21

| | Parameters for analyzing particle size distribution | | | | |
|---|---|---|---|---|---|
| | d(0.1) (μm) | d(0.5) (μm) | d(0.9) (μm) | Surface Weighted Mean D[3,2], (μm) | Volume Weighted Mean D[4,3], (μm) |
| A-1 (Comparative Example 3) | 4.132 | 24.862 | 72.896 | 9.022 | 32.439 |
| A-2 (Comparative Example 4) | 255.596 | 449.893 | 784.560 | 412.188 | 489.297 |
| B-1 (Comparative Example 3, After recrystallization in ethanol) | 2.577 | 10.710 | 34.639 | 5.460 | 15.171 |
| B-2 (Comparative Example 4, After recrystallization in ethanol) | 2.783 | 12.882 | 46.999 | 6.093 | 19.700 |

As can be seen from the above Table 2 and FIG. 1, tolimidone prepared in Comparative Examples 3 and 4 exhibited non-uniform particle size distribution, and the particle sizes showed large difference according to the batch and thus the reproducibility of the particle size distribution was also poor. However, after recrystallization in ethanol, the particle size distribution was uniform. In case of tolimidone prepared in Example 4 after recrystallization in ethanol, the particle size distribution was similar with those of B-1 and B-2.

Experimental Example 3

Purity Measurement

Tolimidone prepared in Comparative Example 3 and tolimidone prepared in Example 4 after recrystallization in ethanol were analyzed by HPLC with the following conditions, and the results are shown in FIGS. 2 and 3.

Column: Agilent ZORBAX Eclipse Plus C18 (4.6×250 mm, 5 μm)
Detection wavelength: 274 nm
Column temperature: 30° C.
Flow rate: 2 mL/min
Mobile phase solvent: Analyzed with concentration gradient condition using 0.1% phosphoric acid-purified water as Solvent A and 100% acetonitrile as Solvent B As can be seen from FIGS. 2 and 3, tolimidone prepared in Comparative Example 3 contained impurities, but it could be confirmed that most of the impurities were removed through recrystallization in ethanol.

The invention claimed is:

1. A method for preparing tolimidone, comprising:
   (i) reacting the compound of formula 6 and the compound of formula 5 in the presence of a tetra-substituted ammonium salt catalyst to prepare the compound of formula 4;
   (ii) conducting Vilsmeir reaction for the prepared compound of formula 4 to prepare the compound of formula 3;
   (iii) refluxing with agitation the prepared compound of formula 3 together with urea and an alkoxide base to prepare the salt compound of formula 2; and
   (iv) desalting the prepared salt compound of formula 2 to obtain tolimidone of formula 1 and recrystallizing the obtained tolimidone with an alcohol that corresponds to the alkoxide base:

[Formula 6]
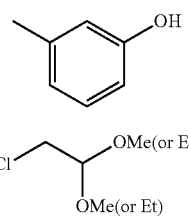

[Formula 5]
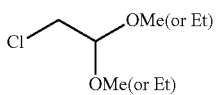

[Formula 4]
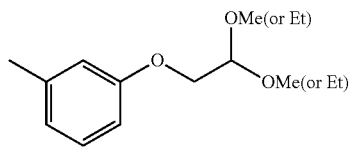

[Formula 3]
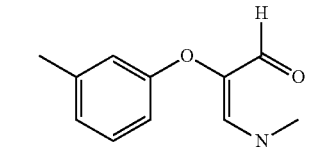

[Formula 2]
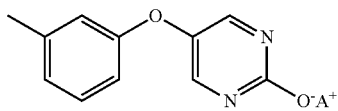

[Formula 1]
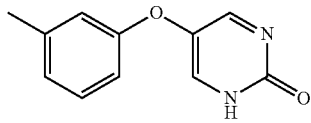

wherein $A^+$ is a cation of the alkoxide base.

2. The method according to claim 1, wherein the tetra-substituted ammonium salt is tetra-alkyl ammonium salt.

3. The method according to claim 2, wherein the tetra-alkyl ammonium salt is tetra-alkyl ammonium halide salt.

4. The method according to claim 3, wherein the tetra-alkyl ammonium halide salt is tetrabutyl ammonium bromide.

5. The method according to claim 1, wherein the tetra-substituted ammonium salt catalyst reaction of said step (i) is conducted in a hydrocarbon solvent in the presence of a hydroxide base.

6. The method according to claim 5, wherein the hydrocarbon solvent is an aromatic hydrocarbon solvent.

7. The method according to claim 6, wherein the aromatic hydrocarbon solvent is toluene.

8. The method according to claim 5, wherein the hydroxide base is potassium hydroxide.

9. The method according to claim 1, wherein the tetra-substituted ammonium salt catalyst reaction of said step (i) is conducted at a temperature of 100 to 120° C.

10. The method according to claim 1, wherein the alkoxide base is sodium ethoxide.

11. The method according to claim 10, wherein the salt compound of formula 2 is the sodium salt compound of formula 7:

[Formula 7]
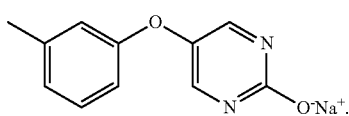

12. The method according to claim 1, wherein the alcohol that corresponds to the alkoxide base is ethanol.

13. The method according to claim 1, wherein the particle size distribution d(0.5) of the prepared tolimidone is 5-30 μm.

* * * * *